United States Patent
Chen et al.

(10) Patent No.: US 11,891,400 B2
(45) Date of Patent: Feb. 6, 2024

(54) PYRAZOLO[1,5-A]PYRIMIDINE-3-CARBOXAMIDE DERIVATIVES USEFUL IN THE TREATMENT OF PSORIASIS AND SYSTEMIC LUPUS ERYTHEMATOSUS

(71) Applicant: Eli Lilly and Company, Indianapolis, IN (US)

(72) Inventors: Zhaogen Chen, Carmel, IN (US); Jon Andre Erickson, Carmel, IN (US); Gaiying Zhao, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 535 days.

(21) Appl. No.: 17/268,644

(22) PCT Filed: Sep. 4, 2019

(86) PCT No.: PCT/US2019/049448
§ 371 (c)(1),
(2) Date: Feb. 16, 2021

(87) PCT Pub. No.: WO2020/055636
PCT Pub. Date: Mar. 19, 2020

(65) Prior Publication Data
US 2021/0188861 A1 Jun. 24, 2021

Related U.S. Application Data

(60) Provisional application No. 62/728,913, filed on Sep. 10, 2018.

(51) Int. Cl.
*C07D 487/04* (2006.01)
*C07D 487/02* (2006.01)
*A61P 17/06* (2006.01)
*A61P 37/00* (2006.01)

(52) U.S. Cl.
CPC ............ *C07D 487/04* (2013.01); *A61P 17/06* (2018.01); *A61P 37/00* (2018.01); *C07D 487/02* (2013.01)

(58) Field of Classification Search
CPC .. C07D 487/02; C07D 487/04; C07D 487/00; A61P 17/06; A61P 37/00
See application file for complete search history.

(56) References Cited

U.S. PATENT DOCUMENTS

| 7,557,110 | B2 | 7/2009 | Kataoka et al. |
| 7,645,762 | B2 | 1/2010 | Paruch et al. |
| 8,637,526 | B2 | 1/2014 | Blaney et al. |
| 8,921,380 | B2 | 12/2014 | Tanimoto et al. |
| 10,273,237 | B2 | 4/2019 | Liu et al. |
| 11,634,423 | B2 * | 4/2023 | Bleisch .................. A61P 37/00 514/259.3 |
| 2006/0089499 | A1 | 4/2006 | Gebauer et al. |
| 2016/0304524 | A1 | 10/2016 | Liu et al. |
| 2019/0225620 | A1 | 7/2019 | Spergel et al. |

FOREIGN PATENT DOCUMENTS

| WO | 2004/022561 A1 | 3/2004 |
| WO | 2004/026229 A2 | 4/2004 |
| WO | 2004/076458 A1 | 9/2004 |
| WO | 2005/077954 A2 | 8/2005 |
| WO | 2010/051549 A1 | 5/2010 |
| WO | 2012/078855 A1 | 6/2012 |
| WO | 2017/087590 A1 | 5/2017 |
| WO | 2018/093968 A1 | 5/2018 |
| WO | 2019/023468 A1 | 1/2019 |
| WO | 2020/055636 A1 | 3/2020 |

OTHER PUBLICATIONS

R. Moslin, et al., MedChemComm, vol. 8(4), pp. 700-712 (Apr. 2017).
Novinson, et al, "Synthesis of Antifungal Properties of Certain 7-Alkylaminopyrazolo[1,5-a]pyrimidines," J Med Chem, vol. 20(2), pp. 296-299 (1977).
Shiota, et al., "Synthesis and Structure-Activity Relationship of a New Series of Potent Angiotensin II Receptor Antagonists: Pyrazolo[1,5-a]pyrimidine Derivatives," Chem Pharm Bull, vol. 47(7), pp. 928-938 (1999).

* cited by examiner

*Primary Examiner* — Samira J Jean-Louis
*Assistant Examiner* — Dawanna Shar-Day White
(74) *Attorney, Agent, or Firm* — Robert D. Shereda

(57) ABSTRACT

The present invention provides a compound of Formula I: wherein R is methyl or ethyl; or a pharmaceutically acceptable salt thereof useful for treating psoriasis or systemic lupus erythematosus.

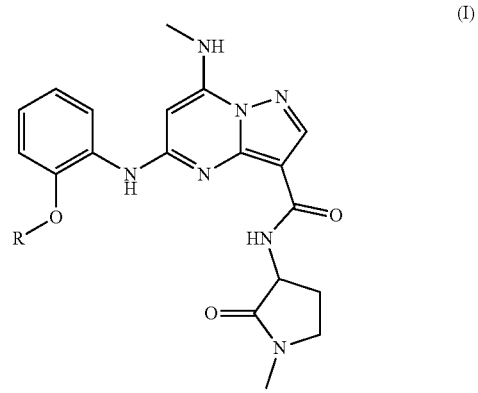

(I)

11 Claims, No Drawings

PYRAZOLO[1,5-A]PYRIMIDINE-3-CARBOXAMIDE DERIVATIVES USEFUL IN THE TREATMENT OF PSORIASIS AND SYSTEMIC LUPUS ERYTHEMATOSUS

The present invention relates to certain novel compounds that bind to the pseudokinase domain (JH2) of TYK2 and inhibit certain cytokine signaling, in particular IL-23 and IFNα signaling, to pharmaceutical compositions comprising the compounds, to methods of using the compounds to treat certain autoimmune diseases, such as psoriasis, and to intermediates and processes useful in the synthesis of the compounds.

The present invention is in the field of treatment of psoriasis and/or other autoimmune diseases thought to be mediated by TYK2 signaling of certain proinflammatory cytokines (See e.g., J. S. Tokarski, et al., *J. Biol. Chem.*, vol. 290(17), pages 11061-11074 (2015)). Psoriasis is a chronic skin disease, which is estimated to affect approximately 2% of the general population. Treatment options for psoriasis include, for example, topical treatments, such as corticosteroids, phototherapy, such as ultraviolet B (UVB) light, and systemic treatments, such as methotrexate and apremilast. Unfortunately, such agents do not always provide effective treatment and can be associated with various untoward side effects. Thus, there is an unmet need in the treatment of autoimmune diseases, such as psoriasis and systemic lupus erythematosus, and new treatment options are desired.

WO 2017/087590 discloses certain imidazopyridazine compounds useful for the treatment of autoimmune conditions, such as psoriasis or systemic lupus erythematosus, through modulation of IL-12, IL-23, and/or IFNα by acting on TYK2 to cause signal transduction inhibition. U.S. Pat. No. 7,557,110 discloses certain pyrazolo[1,5-a]pyrimidine derivatives as kinase inhibitors useful for treating kinase mediated disorders, such as inflammatory disease and autoimmune disease. Certain imidazo[1,2-b]pyridazine TYK2 pseudokinase ligands are disclosed by R. Moslin, et al., *Med. Chem. Commun.*, vol. 8, pages 700-712 (2017) as potent and selective inhibitors of TYK2 signaling.

Additional compounds that act on the TYK2 JH2 domain and inhibit signal transduction of IL-23 and IFNα are desired. The present invention provides certain novel compounds that bind to the TYK2 JH2 domain. In addition, the present invention provides certain novel compounds that inhibit IL-23 and IFNα signaling. Thus, the present invention provides certain novel compounds that are useful for treating autoimmune diseases, such as psoriasis and systemic lupus erythematosus.

Accordingly, the present invention provides a compound of Formula I

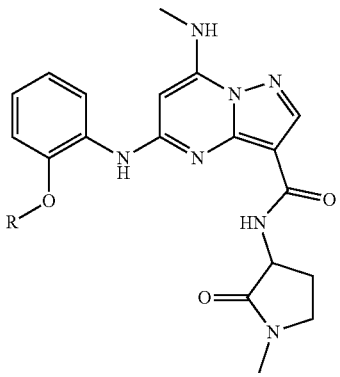

Formula I wherein R is methyl or ethyl;
or a pharmaceutically acceptable salt thereof.

The present invention also provides a method of treating psoriasis in a patient in need of such treatment, comprising administering to the patient an effective amount of a compound of Formula I, or a pharmaceutically acceptable salt thereof. The present invention further provides a method of treating systemic lupus erythematosus in a patient in need of such treatment, comprising administering to the patient an effective amount of a compound of Formula I, or a pharmaceutically acceptable salt thereof. The present invention further provides a method of treating a disease selected from the group consisting of inflammatory bowel disease, ulcerative colitis, Crohn's Disease, psoriatic arthritis, rheumatoid arthritis, alopecia areata, atopic dermatitis, axial spondyloarthritis, and multiple sclerosis in a patient in need of such treatment, comprising administering to the patient an effective amount of a compound of Formula I, or a pharmaceutically acceptable salt thereof.

Furthermore, this invention provides a compound of Formula I, or a pharmaceutically acceptable salt thereof for use in therapy, in particular for use in treating psoriasis. In addition, this invention provides a compound of Formula I, or a pharmaceutically acceptable salt thereof, for use in treating systemic lupus erythematosus. The invention also provides a compound of Formula I, or a pharmaceutically acceptable salt thereof, for use in treating a disease selected from the group consisting of inflammatory bowel disease, ulcerative colitis, Crohn's Disease, psoriatic arthritis, rheumatoid arthritis, alopecia areata, atopic dermatitis, axial spondyloarthritis, and multiple sclerosis.

This invention also provides the use of a compound of Formula I, or a pharmaceutically acceptable salt thereof, for the manufacture of a medicament for treating psoriasis. In addition, this invention provides the use of a compound of Formula I, or a pharmaceutically acceptable salt thereof, for the manufacture of a medicament for treating systemic lupus erythematosus. The invention also provides the use of a compound of Formula I, or a pharmaceutically acceptable salt thereof, for the manufacture of a medicament for treating a disease selected from the group consisting of inflammatory bowel disease, ulcerative colitis, Crohn's Disease, psoriatic arthritis, rheumatoid arthritis, alopecia areata, atopic dermatitis, axial spondyloarthritis, and multiple sclerosis.

The invention further provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients. This invention also encompasses novel intermediates and processes for the synthesis of the compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. Compounds of the present invention are prepared as unit dosage forms to provide a dosage per day that falls within the range of about 0.005 mg/kg to about 8 mg/kg of body weight.

The compounds of the present invention are formulated as pharmaceutical compositions administered by any route which makes the compound bioavailable. Most preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

The compound of Formula I, or a pharmaceutically acceptable salt thereof, is particularly useful in the treatment methods of the invention, with all configurations, enantiomers and mixtures thereof, including racemates, being contemplated within the scope of the invention, although certain configurations are preferred. The following paragraphs describe such configurations. It will be understood that these preferences are applicable both to the treatment methods and to the compounds of the invention.

Compounds of the present invention include:

Formula Ia

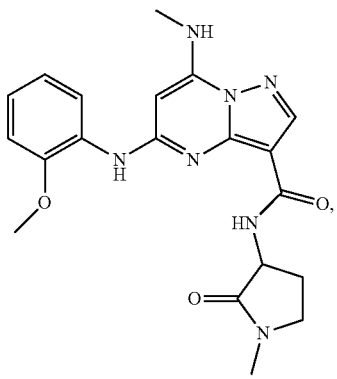

Formula Ia(i)

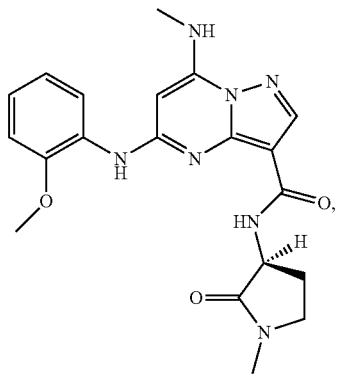

Formula Ia(ii)

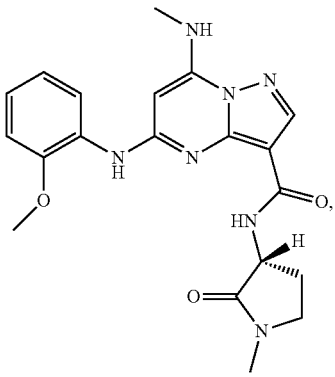

Formula Ib

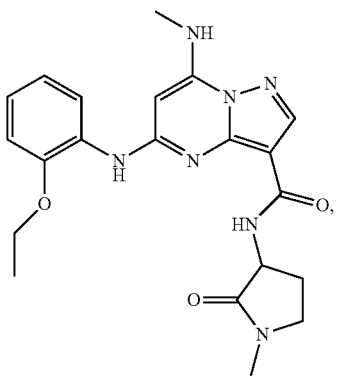

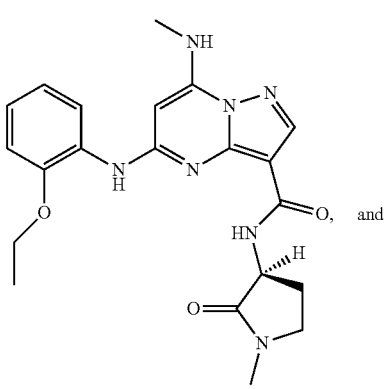

Formula Ib(i)

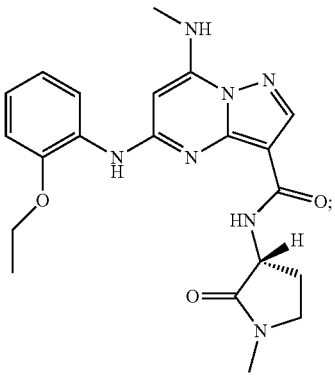

Formula Ib(ii)

and the pharmaceutically acceptable salts thereof.

The compounds of Formula Ia(ii) and Formula Ib(ii) are preferred, with the compound of Formula Ia(ii) and the pharmaceutically acceptable salts thereof being particularly preferred.

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "Greene's *Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See, for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of a compound of the invention can be formed, for example, by reaction of an appropriate free base of a compound of the invention, an appropriate pharmaceutically acceptable acid in a suitable solvent such as diethyl ether under standard conditions well known in the art. Additionally, the formation of such salts can occur simultaneously upon deprotection of a nitrogen protecting group. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "BOP" refers to (Benzotriazol-1-yloxy)tris(dimethylamino)phosphonium hexafluorophosphate; "BrettPhos" refers to dicyclohexyl[3,6-dimethoxy-2',4',6'-tris(1-methylethyl)[1,1'-biphenyl]-2-yl]phosphine; "t-BuOH" refers to t-butanol and t-butyl alcohol; "BSA" refers to Bovine Serum Albumin; "CDI" refers 1,1'-carbonyldiimidazole; "DCC" refers to 1,3-dicyclohexylcarbodiimide; "DCM" refers to dichloromethane; "DEM" refers to diethylmalonate; "DIC" refers to 1,3-diisopropylcarbodiimide; "DIEA" refers to N,N-diisopropylethylamine; "DMAP" refers to dimethylaminopyridine; "DMEM" refers to Dulbecco's Modified Eagle's Medium; "DMF" refers to N,N-dimethylformamide; "DMSO" refers to dimethyl sulfoxide; "DPPA" refers to diphenylphosphoryl azide; "EDCI" refers to 1-(3-dimethylaminopropyl)-3-ethylcarbodiimide hydrochloride; "EtOAc" refers to ethyl acetate; "EtOH" refers to ethanol and ethyl alcohol; "FBS" refers to Fetal Bovine Serum; "HATU" refers to 1-[bis(dimethylamino)methylene]-1H-1,2,3-triazolo[4,5-b]pyridinium 3-oxid hexafluorophosphate; "HBTU" refers to (1H-benzotriazol-1-yloxy)(dimethylamino)-N,N-dimethylmethaniminium hexafluorophosphate; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "IFNα" refers to interferon alpha; "IL-12" refers to interleukin 12; "IL-23" refers to interleukin 23; "IPA" refers to isopropanol and isopropyl alcohol; "JAK" refers to Janus kinase; "LiHMDS" refers to lithium hexamethyldisilazide; "MeI" refers to methyl iodide; "MeNH$_2$" refers to methylamine; "MeOH" refers to methanol and methyl alcohol; "MTBE" refers to methyl tert-butyl ether; "NaOEt" refers to sodium ethoxide; "Ni NTA" refers to nickel-nitrilotriacetic acid; "PBS" refers to Phosphate Buffered Saline; "Pd(OAc)$_2$" refers to palladium (II) acetate; "PyBOP" refers to (benzotriazol-1-yl-oxytripyrrolidinophosphoniun hexafluorophosphate); "PyBrOP" refers to bromo(tri-pyrrolidinyl)phosphoniumhexafluorophosphate; "RPM" refers to revolutions per minute; "RPMI" refers to Roswell Park Memorial Institute; "SPA" refers to scintillation proximity assay; "T3P" refers to 2,4,6-tripropyl-1,3,5,2,4,6-trioxatriphosphorinane-2,4,6-trioxide; "TEA" refers to triethylamine; "TFA" refers to trifluoroacetic acid; "THF" refers to tetrahydrofuran; "TYK2" refers to tyrosine kinase 2; "UVB" refers to ultraviolet B; "STAT" refers to signal transducer and activator of transcription protein; and "YSI" refers to yttrium silicate.

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1
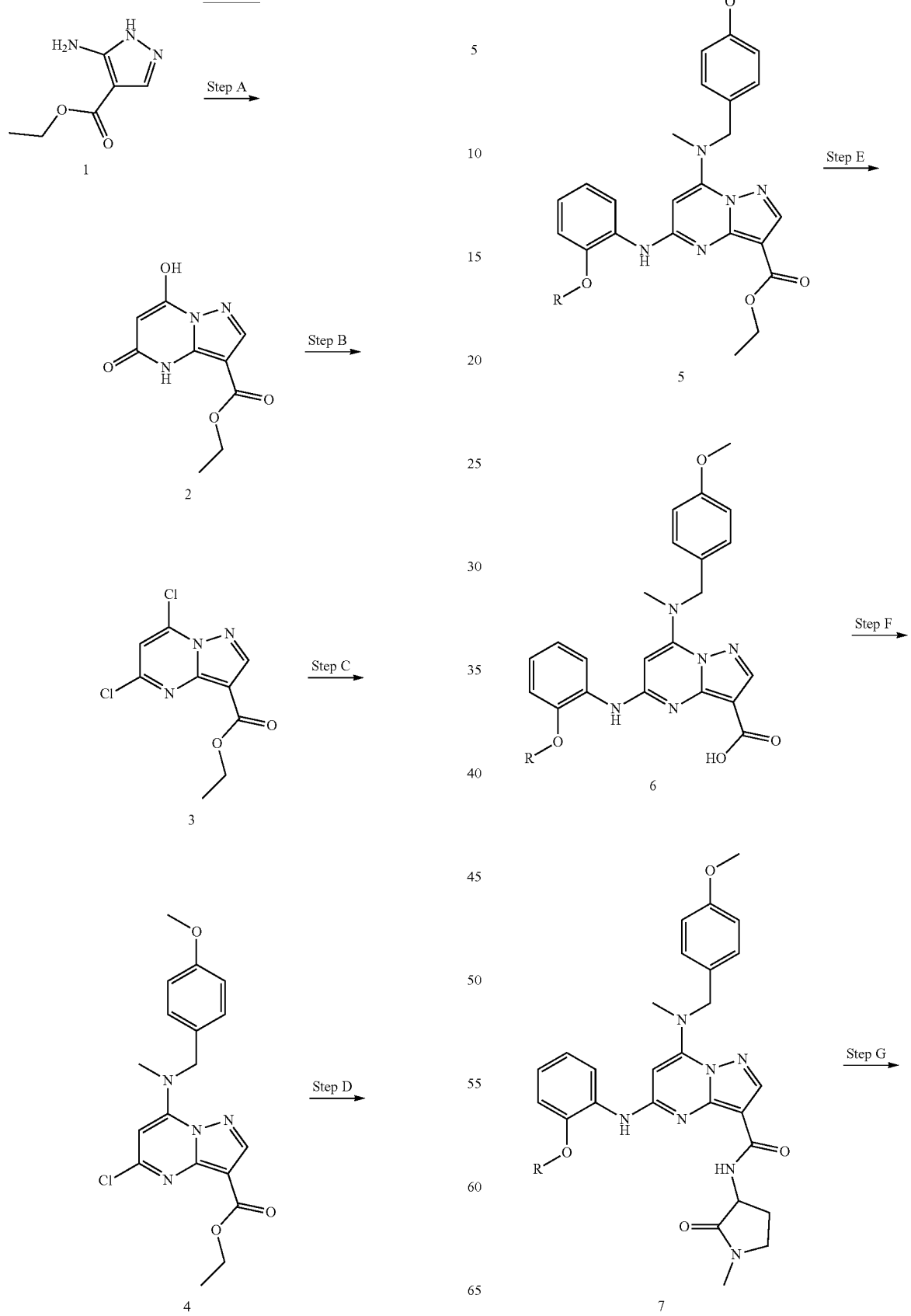

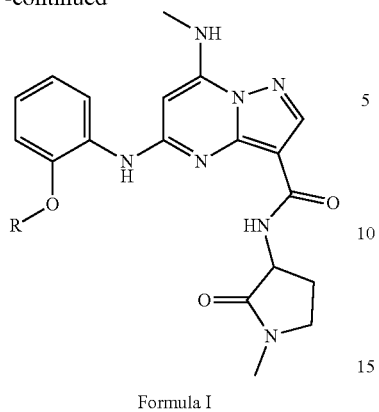

Formula I

Scheme 1, step A depicts the addition of DEM to compound (1) and the subsequent cyclization to compound (2) using a suitable base such as NaOEt or potassium t-butoxide at around 80° C. in a solvent such as EtOH.

In step B, the 7-hydroxy and 5-oxo groups of compound (2) can be chlorinated using a suitable chlorine source such as POCl₃ and a suitable organic base such as pyridine at about 50-100° C. in a suitable solvent such as acetonitrile to give compound (3).

In step C, a selective nucleophilic aromatic substitution on the 7-chloro group of compound (3) can be performed under conditions well known in the art using a nucleophile such as 1-(4-methoxyphenyl)-N-methyl-methanamine and a suitable organic base such as DIEA in a suitable solvent such as 1,4-dioxane at ambient temperature to give compound (4).

In step D, a Buchwald coupling can be performed under conditions well known in the art on compound (4) with amines such as 2-methoxyaniline or 2-ethoxyaniline to form compound (5) using a suitable catalyst and ligand combination such as Pd(OAc)₂ and BrettPhos, and a suitable base such as potassium carbonate in a solvent such as 1,4-dioxane with microwave heating at around 120° C.

Compound (5) can be treated with aqueous NaOH in solvents such as 1,4-dioxane and EtOH at about 90° C. to give compound (6) through basic hydrolysis of the ester as shown in step E.

In step F, an amide coupling can be performed between compound (6) and an amine such as 3-amino-1-methyl-pyrrolidin-2-one using a suitable organic base such as DIEA and a suitable coupling agent such as BOP in a suitable solvent such as DMF to give compound (7). One skilled in the art will recognize that there are several appropriate methods for amide formation resulting from the reaction of a carboxylic acid and an amine. For example, the reaction of the amine compound with an appropriate carboxylic acid in the presence of a coupling reagent with or without an organic base such as DIEA or TEA can provide a compound of step F. Coupling reagents include carbodiimides, such as DCC, DIC, EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may be used to enhance the reaction.

In step G, compound (7) is deprotected under standard conditions using a suitable acid such as TFA in a suitable solvent such as DCM to give a compound of Formula I.

Scheme 2 provides an additional synthesis of the racemic compound of Formula I.

Scheme 2

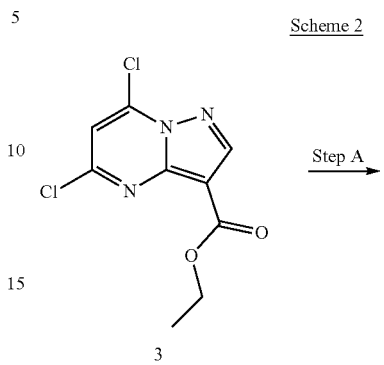

3

Step A

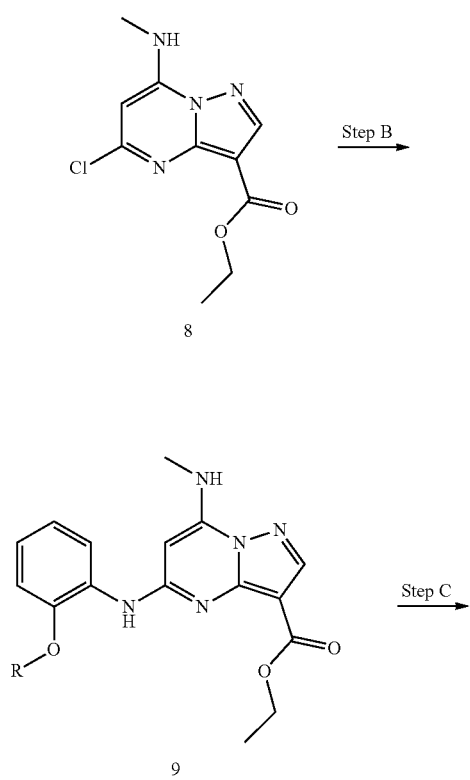

8

Step B

9

Step C

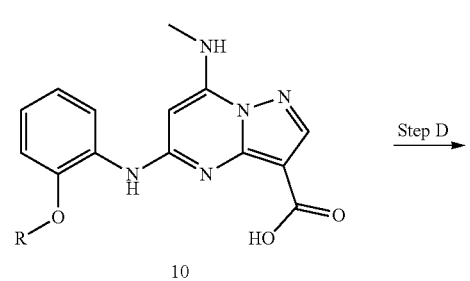

10

Step D

-continued

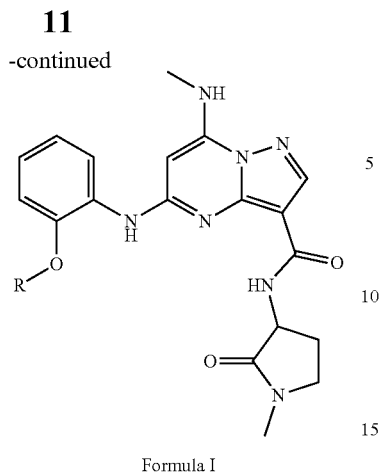

Formula I

In scheme 2, step A, a selective nucleophilic aromatic substitution on the 7-chloro group of compound (3) can be performed under conditions well known in the art using an appropriate nucleophile such as MeNH₂ in a suitable solvent such as THF at ambient temperature to give compound (8).

In step B, a Buchwald coupling can be performed on compound (8) under standard microwave conditions with amines such as 2-methoxyaniline or 2-ethoxyaniline to form compound (9) using a suitable catalyst and ligand system such as allylpalladium(II) chloride dimer and (R)-(+)-2,2'-bis(diphenylphosphino)-1,1'-binaphthyl with a suitable base such as potassium carbonate in an appropriate solvent system such as 1,4-dioxane, 2-methyl-2-butanol, and acetic acid with heating at 105° C.

Compound (9) can be treated with a suitable base such as aqueous lithium hydroxide in a suitable solvent such as EtOH at about 90° C. to give compound (10) through basic hydrolysis of the ester as shown in step C.

Step D depicts the formation of Formula I through an amide coupling under conditions well known in the art, as described generally in Scheme 1, step F, between compound (10) and an amine such as 3-amino-1-methyl-pyrrolidin-2-one using a suitable organic base such as DIEA and a suitable coupling agent such as EDCI with a suitable additive such as HOBt in a solvent such as THF.

-continued

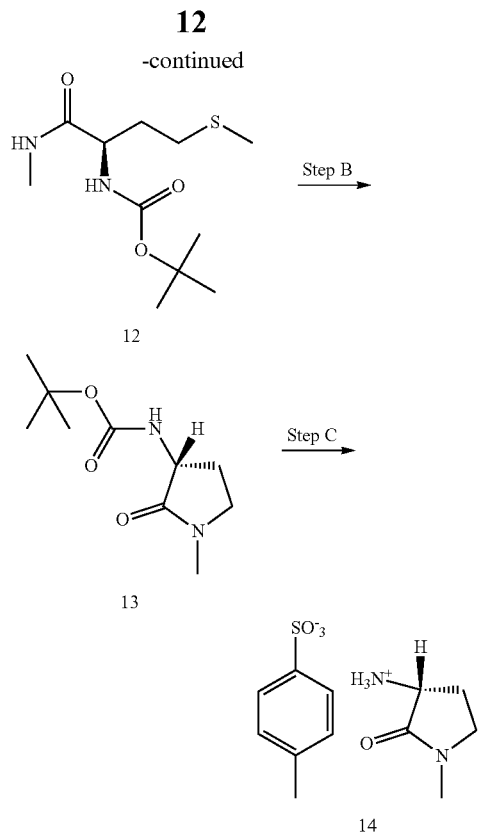

In scheme 3, step A, the formation of compound (12) is shown as an amide coupling under conditions well known in the art, as described generally in Scheme 1, step F, between compound (11) and MeNH₂ using a suitable organic base such as DIEA and a suitable coupling agent such as HATU in a solvent such as DMF at 0-22° C.

In step B, addition of MeI to compound (12) to form a dimethylsulfonium iodide salt followed by treatment with a suitable base such as LiHMDS in a suitable solvent such as THF at 0-22° C. can be used to give the cyclized compound (13).

In step C, compound (13) is deprotected under standard conditions using a suitable acid such as 4-methylbenzene-sulfonic acid in a suitable solvent such as acetonitrile at around 55° C., followed by addition of a solvent such as MTBE to precipitate compound (14).

Scheme 3

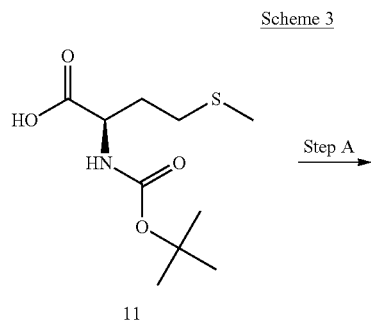

Scheme 4

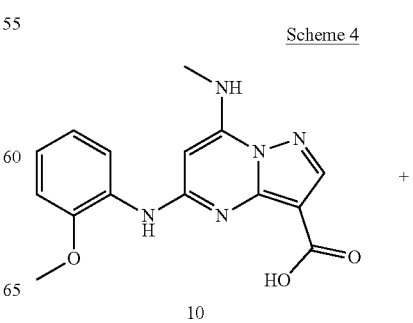

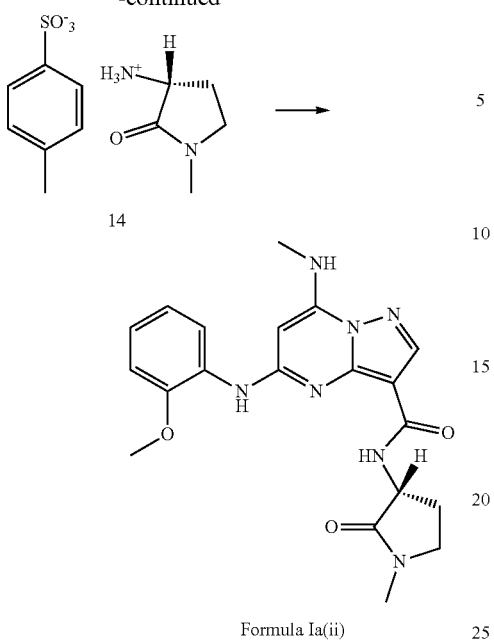

Formula Ia(ii)

In scheme 4 the formation of Formula Ia(ii) is depicted as an amide coupling under conditions well known in the art, as described generally in Scheme 1, step F, between compound (10) and compound (14) using a suitable organic base such as pyridine and a suitable coupling agent such as T3P in a solvent such as EtOAc at around 80° C.

Preparation 1

Ethyl 7-hydroxy-5-oxo-4H-pyrazolo[1,5-a]pyrimidine-3-carboxylate

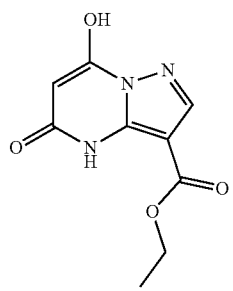 [SMILES: CCOC(=O)c1cnn2c(O)cc(=O)[nH]c12]

Scheme 1, step A: Ethyl 5-amino-1H-pyrazole-4-carboxylate (12.5 g, 80.6 mmol), and DEM (18.5 mL, 121 mmol) are dissolved in EtOH (90 mL). To this mixture is added NaOEt (21 m % in EtOH, 45.1 ml, 121 mmol) and the reaction is stirred at 90° C. for 24 hours. After this time, the reaction is cooled to ambient temperature. The mixture is then made acidic with 5 N HCl aqueous solution and the resulting precipitate is filtered to give the title compound as a white solid (11.7 g, 65.1%). ES/MS m/z 224 (M+H).

Alternate Preparation 1

Scheme 1, step A: To a solution of ethyl 5-amino-1H-pyrazole-4-carboxylate (400 g, 2.58 mol) and DEM (584 mL, 3.87 mol) in EtOH (6.00 L) is added potassium t-butoxide (578 g, 5.16 mol) at 25° C. under nitrogen. The solution is stirred at 80° C. for 12 hours and then the reaction is cooled to 22° C. The reaction mixture is diluted with 0.1 N HCl (2 L) and the pH is adjusted to 3 with 5 N HCl. The mixture is filtered and the filter cake is washed with water (800 mL). The solid is dried under vacuum to constant weight to give the title compound as an off-white solid (460 g, 81%). ES/MS m/z 224 (M+H).

Preparation 2

Ethyl 5,7-dichloropyrazolo[1,5-a]pyrimidine-3-carboxylate

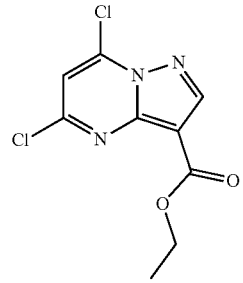 [SMILES: CCOC(=O)c1cnn2c(Cl)cc(Cl)nc12]

Scheme 1, step B: Ethyl 7-hydroxy-5-oxo-4H-pyrazolo[1,5-a]pyrimidine-3-carboxylate (11.7 g, 52.4 mmol) is suspended in acetonitrile (50 mL) and purged with nitrogen for 5 minutes. To this mixture is added POCl$_3$ (14.8 ml, 157 mmol) followed by pyridine (4.28 mL, 52.4 mmol) at 50° C. and then the reaction is stirred at 100° C. for 5 hours. After this time, the reaction is cooled to ambient temperature and poured into an ice/water mixture. This mixture is neutralized with saturated aqueous sodium bicarbonate solution and the resulting precipitate is filtered to give the title compound as a white solid (13 g, 95.3%). ES/MS m/z ($^{35}$Cl/$^{37}$Cl) 260/262 [M+H]$^+$.

Alternate Preparation 2

Scheme 1, step B: To a suspension of ethyl 7-hydroxy-5-oxo-4H-pyrazolo[1,5-a]pyrimidine-3-carboxylate (400 g, 1.79 mol) in acetonitrile (2 L), POCl$_3$ (416 mL, 4.48 mol) and pyridine (217 ml, 2.69 mol) are added drop-wise at 50° C. under nitrogen. The reaction is stirred at 80° C. for 12 hours. The reaction mixture is evaporated and the residue is poured into water (2 L). The reaction mixture is filtered and the solid is washed with water (800 mL). The solid is dried under vacuum to constant weight to give the title compound as an orange solid (360 g, 66%). ES/MS m/z ($^{35}$Cl/$^{37}$Cl) 260/262 [M+H]$^+$.

Preparation 3

Ethyl 5-chloro-7-[(4-methoxyphenyl)methyl-methyl-amino]pyrazolo[1,5-a]pyrimidine-3-carboxylate

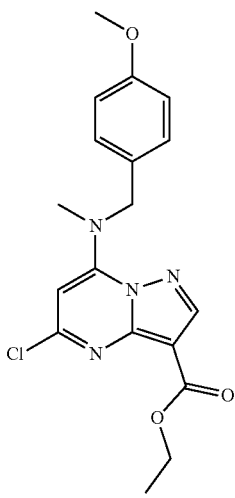 [SMILES: CCOC(=O)c1cnn2c(N(C)Cc3ccc(OC)cc3)cc(Cl)nc12]

Scheme 1, step C: Ethyl 5,7-dichloropyrazolo[1,5-a]pyrimidine-3-carboxylate (5 g, 19.2 mmol) is dissolved in 1,4-dioxane (40 mL). To this mixture is added 1-(4-methoxyphenyl)-N-methyl-methanamine (3.5 g, 20 mmol) followed by DIEA (6.7 mL, 38.4 mmol) and the reaction is stirred at ambient temperature for 2 hours. After this time, the reaction is quenched with water (100 mL) and extracted with EtOAc (3×100 mL). The combined organics are then dried over magnesium sulfate, filtered, and evaporated. This residue is purified via silica gel chromatography (0-70% EtOAc in hexanes) to give the title compound as a thick clear oil which solidifies to a white solid upon standing (3.55 g, 49.3%). ES/MS m/z ($^{35}Cl/^{37}Cl$) 375/377 [M+H]$^+$.

Preparation 3a

Ethyl 5-chloro-7-(methylamino)pyrazolo[1,5-a]pyrimidine-3-carboxylate

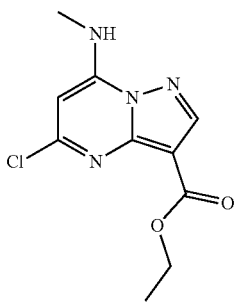 [SMILES: CCOC(=O)c1cnn2c(NC)cc(Cl)nc12]

Scheme 2, step A: Ethyl 5,7-dichloropyrazolo[1,5-a]pyrimidine-3-carboxylate (50.0 g, 192 mmol) is added to THF (250 mL) and the solution is cooled to 10° C. Then a solution of MeNH$_2$ (33% w/w in ethanol) (79 mL, 634 mmol) is added, keeping the temperature below 20° C. The reaction mixture is stirred and warmed to 22° C. and stirred for 4 hours. Then water (300 mL) is added and the mixture is stirred for an additional 1 hour.

The resulting solids are collected by filtration and washed with a THF/water mixture (2:3) (100 mL) and water (400 mL). The solid is then dried under vacuum (10 mbar/50° C.) to constant weight to give the title compound as pale brown solid (49.5 g, 90%). ES/MS m/z ($^{35}Cl/^{37}Cl$) 255/257 [M+H]$^+$.

Preparation 4

Ethyl 5-(2-methoxyanilino)-7-[(4-methoxyphenyl)methyl-methyl-amino]pyrazolo[1,5-a]pyrimidine-3-carboxylate

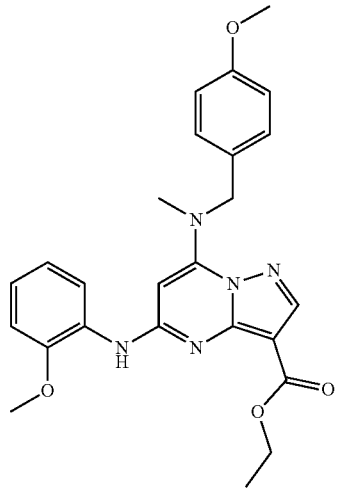 [SMILES: CCOC(=O)c1cnn2c(N(C)Cc3ccc(OC)cc3)cc(Nc3ccccc3OC)nc12]

Scheme 1, step D: To each of four microwave vials, ethyl 5-chloro-7-[(4-methoxyphenyl)methyl-methyl-amino]pyrazolo[1,5-a]pyrimidine-3-carboxylate (2.5 g, 6.7 mmol) and 2-methoxyaniline (0.9 g, 7.3 mmol) is dissolved in 1,4-dioxane (17 mL). To this mixture is added potassium carbonate (1.4 g, 10 mmol) followed by BrettPhos (0.37 g, 0.67 mmol) and Pd(OAc)$_2$ (0.15 g, 0.67 mmol). The reactions are microwaved to 120° C. for 2 hours. After this time, the reactions are cooled to ambient temperature. The reaction mixtures are combined, filtered through diatomaceous earth, and evaporated. The resulting residue is purified via silica gel chromatography (30-50% EtOAc in hexanes) to give the title compound as an off-white foam (10.8 g, 88.0%). ES/MS m/z 462 (M+H).

The following compound is prepared in a manner essentially analogous to the method of Preparation 4.

TABLE 1

| Prep. No. | Chemical name | Structure | Physical data |
|---|---|---|---|
| 5 | Ethyl 5-(2-ethoxyanilino)-7-[(4-methoxyphenyl)methyl-methyl-amino]pyrazolo[1,5-a]pyrimidine-3-carboxylate | 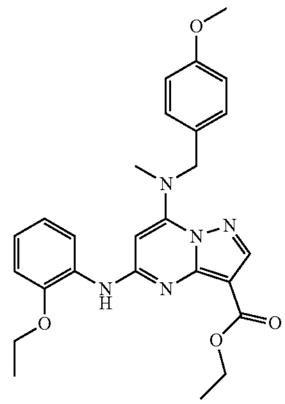 [SMILES: CCOC(=O)c1cnn2c(N(C)Cc3ccc(OC)cc3)cc(Nc3ccccc3OCC)nc12] | ES/MS m/z 476 (M + H). |

TABLE 2

| Prep. No. | Chemical name | Structure | Physical data |
|---|---|---|---|
| 5a | Ethyl 5-(2-ethoxyanilino)-7-(methylamino)pyrazolo[1,5-a]pyrimidine-3-carboxylate | 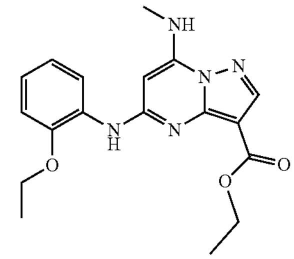 | ES/MS m/z 356 (M + H). |

Preparation 4a

Ethyl 5-(2-methoxyanilino-7-(methylamino)pyrazolo[1,5-a]pyrimidine-3-carboxylate

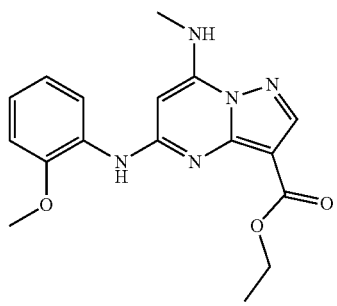 [SMILES: CCOC(=O)c1cnn2c(NC)cc(Nc3ccccc3OC)nc12]

Scheme 2, step B: To a 1 L 3-neck round bottom flask with mechanical stirrer, condenser, and nitrogen inlet, is added ethyl 5-chloro-7-(methylamino)pyrazolo[1,5-a]pyrimidine-3-carboxylate (53.0 g, 197.7 mmol), 2-methoxyaniline (25.1 g, 203.9 mmol) and potassium carbonate (60.0 g, 434.1 mmol) followed by 1,4-dioxane (250 mL) and anhydrous 2-methyl-2-butanol (250 ml). The mixture is stirred and purged with nitrogen for 30 minutes. Then, acetic acid (23.0 mL, 401.4 mmol), allylpalladium(II) chloride dimer (0.4 g, 1.07 mmol), and (R)-(+)-2,2'-bis(diphenylphosphino)-1,1'-binaphthyl (1.37 g, 2.13 mmol) are added, and the nitrogen purge is continued for 15 minutes. The reaction mixture is then heated at 105° C. for 20 hours. After this time, the heating is stopped and water is added (400 mL) in a thin stream. The resulting mixture is cooled to ambient temperature while stirring and then further cooled to 15° C. for 2 hours. The resulting solids are collected by filtration and washed with a water/t-amyl alcohol (9:1) mixture (3×100 mL) and water (150 mL). The solid is dried under vacuum (10 mbar/35° C.) to constant weight to give the title compound as a beige solid (66.5 g, 95.6%). ES/MS m/z 342 (M+H).

The following compound is prepared in a manner essentially analogous to the method of Preparation 4a.

Preparation 6

5-(2-Methoxyanilino)-7-[(4-methoxyphenyl)methyl-methyl-amino]pyrazolo[1,5-a]pyrimidine-3-carboxylic acid

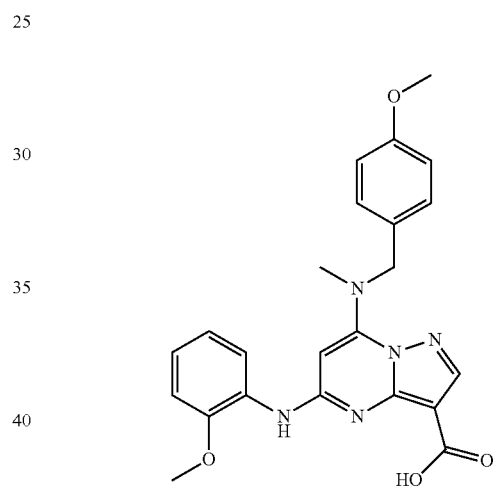

Scheme 1, step E: Ethyl 5-(2-methoxyanilino)-7-[(4-methoxyphenyl)methyl-methyl-amino]pyrazolo[1,5-a]pyrimidine-3-carboxylate (10.8 g, 23.4 mmol) is dissolved in 1,4-dioxane (117 mL) and EtOH (4.7 mL). To this mixture is added 2.5 N aqueous NaOH (37 mL, 93.6 mmol) and the reaction is stirred at 90° C. for 20 hours. After this time, the reaction is cooled to ambient temperature and evaporated to remove the volatile organics. The remaining aqueous solution is then brought to approximately pH 5 with 1 N aqueous HCl and the solid precipitate is extracted with chloroform/IPA (3:1) (3×300 mL). The combined organic layers are dried over anhydrous sodium sulfate, filtered, and evaporated to give the title compound as an off-white solid (9.54 g, 89.9%). ES/MS m/z 434 (M+H).

The following compound is prepared in a manner essentially analogous to the method of Preparation 6.

TABLE 3

| Prep. No. | Chemical name | Structure | Physical data |
|---|---|---|---|
| 7 | 5-(2-Ethoxyanilino)-7-[(4-methoxyphenyl)methyl-methyl-amino]pyrazolo[1,5-a]pyrimidine-3-carboxylic acid | 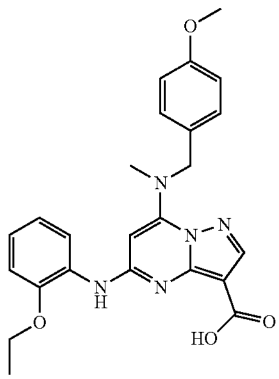 [SMILES: CCOc1ccccc1Nc1cc(N(C)Cc2ccc(OC)cc2)n2ncc(C(=O)O)c2n1] | ES/MS m/z 448 (M + H). |

Preparation 6a 5-(2-Methoxyanilino)-7-(methylamino)pyrazolo[1,5-a]pyrimidine-3-carboxylic

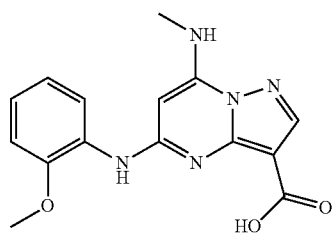 [SMILES: CNc1cc(Nc2ccccc2OC)nc2c(C(=O)O)cnn12]

Scheme 2, step C: A mixture of ethyl 5-(2-methoxyanilino)-7-(methylamino)pyrazolo[1,5-a]pyrimidine-3-carboxylate (5.98 g, 17.3 mmol), EtOH (48 mL), water (30 mL), and lithium hydroxide (1.2 g, 50.0 mmol) is refluxed for 4 hours. After this time, the reaction mixture is cooled to 70° C. and neutralized by adding HCl (10% w/w) to adjust to pH 2. Then, the reaction mixture is cooled to 2° C. and stirred for 2 hours. The resulting solid is collected by filtration and washed with water (30 mL). The solid is dried under vacuum to constant weight to give the title compound as a cream solid (5.55 g, 100%). ES/MS m/z 314 (M+H).

The following compound is prepared in a manner essentially analogous to the method of Preparation 6a.

TABLE 4

| Prep. No. | Chemical name | Structure | Physical data |
|---|---|---|---|
| 7a | 5-(2-Ethoxyanilino)-7-(methylamino)pyrazolo[1,5-a]pyrimidine-3-carboxylic acid | 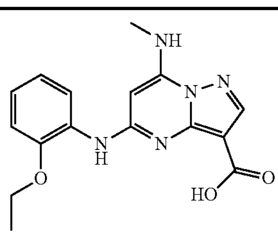 | ES/MS m/z 328 (M + H). |

Preparation 8

5-(2-Methoxyanilino)-7-[(4-methoxyphenyl)methyl-methyl-amino]-N-[rac-1-methyl-2-oxo-pyrrolidin-3-yl]pyrazolo[1,5-a]pyrimidine-3-carboxamide

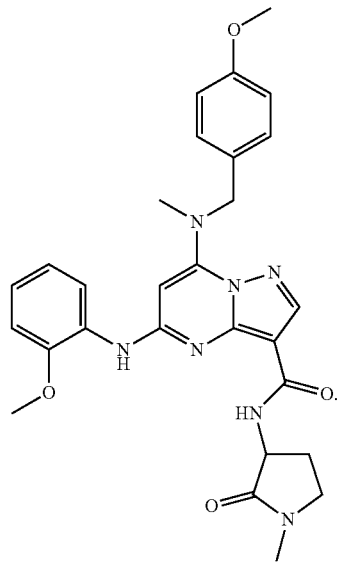 [SMILES: COc1ccc(CN(C)c2cc(Nc3ccccc3OC)nc3c(C(=O)NC4CCN(C)C4=O)cnn23)cc1]

Scheme 1, step F: To a mixture of 5-(2-methoxyanilino)-7-[(4-methoxyphenyl)methyl-methyl-amino]pyrazolo[1,5-a]pyrimidine-3-carboxylic acid (0.30 g, 0.69 mmol) and racemic 3-amino-1-methyl-pyrrolidin-2-one (0.095 g, 0.83 mmol) in DMF (3.5 mL) is added BOP (0.41 g, 0.93 mmol) and DIEA (0.48 mL, 2.77 mmol). The reaction mixture is stirred at ambient temperature under nitrogen for 60 hours. After this time, the reaction is quenched with saturated aqueous ammonium chloride solution (30 mL) and extracted with EtOAc (50 mL). The organic layer is washed with water and saturated aqueous NaCl solution, dried over anhydrous sodium sulfate, filtered, and evaporated. This residue is purified via silica gel chromatography (24% MeOH in DCM) to give the title compound (0.30 g, 83.2%). ES/MS m/z 530 (M+H).

The following compound is prepared in a manner essentially analogous to the method of Preparation 8.

TABLE 5

| Prep. No. | Chemical name | Structure | Physical data |
|---|---|---|---|
| 9 | 5-(2-Ethoxyanilino)-7-[(4-methoxyphenyl)methyl-methyl-amino]-N-[rac-1-methyl-2-oxo-pyrrolidin-3-yl]pyrazolo[1,5-a]pyrimidine-3-carboxamide | 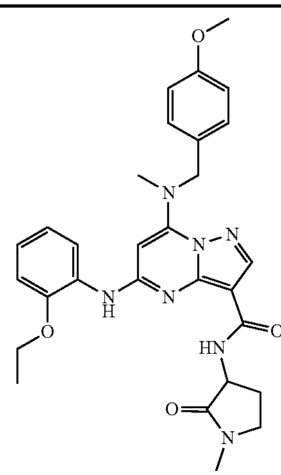 | ES/MS m/z 544 (M + H). |

Preparation 10

5-(2-Methoxyanilino)-7-(methylamino)-N-[rac-1-methyl-2-oxo-pyrrolidin-3-yl]pyrazolo[1,5-a]pyrimidine-3-carboxamide

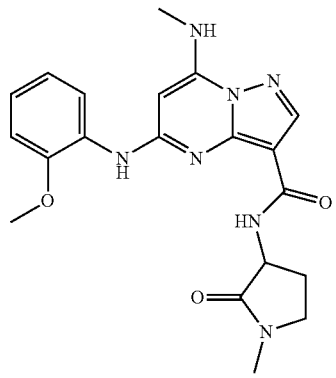 [SMILES: CNc1cc(Nc2ccccc2OC)nc2c(C(=O)NC3CCN(C)C3=O)cnn12]

Scheme 1, step G: A solution of 5-(2-methoxyanilino)-7-[(4-methoxyphenyl)methyl-methyl-amino]-N-[rac-1-methyl-2-oxo-pyrrolidin-3-yl]pyrazolo[1,5-a]pyrimidine-3-carboxamide (0.3 g, 0.58 mmol) in DCM (11.5 mL) and TFA (11.5 mL) is stirred at ambient temperature for 4 hours. After this time, the reaction is evaporated to remove the volatile organics. The residue is treated with DCM (20 mL) and 7 M ammonia in methanol (4 mL). The resulting mixture is stirred for 10 minutes and evaporated. The residue is then purified via silica gel chromatography (2-8% MeOH in DCM) to give the title compound (0.18 g, 74.2%). ES/MS m/z 410 (M+H).

The following compound is prepared in a manner essentially analogous to the method of Preparation 10.

TABLE 6

| Prep. No. | Chemical name | Structure | Physical data |
|---|---|---|---|
| 11 | 5-(2-ethoxyanilino)-7-(methylamino)-N-[rac-1-methyl-2-oxo-pyrrolidin-3-yl]pyrazolo[1,5-a]pyrimidine-3-carboxamide | 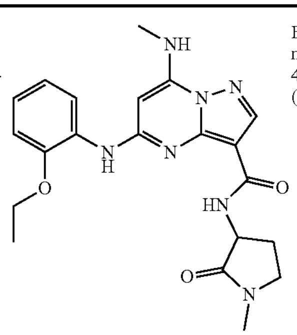 | ES/MS m/z 424 (M + H) |

Alternate Preparation 11

5-(2-Ethoxyanilino)-7-(methylamino)-N-[rac-1-methyl-2-oxo-pyrrolidin-3-yl]pyrazolo[1,5-a]pyrimidine-3-carboxamide

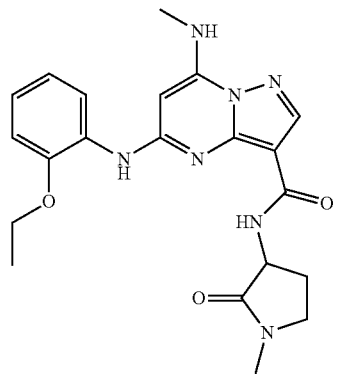 [SMILES: CCOc1ccccc1Nc1cc(NC)n2ncc(C(=O)NC3CCN(C)C3=O)c2n1]

Scheme 2, step D: 5-(2-Ethoxyanilino)-7-(methylamino)pyrazolo[1,5-a]pyrimidine-3-carboxylic acid (4.5 g, 8.9 mmol), racemic 3-amino-1-methyl-pyrrolidin-2-one (1.2 g, 11.0 mmol), and HOBt (1.8 g, 13.0 mmol) are suspended in THF (89 mL). To this mixture is added EDCI (2.6 g, 13.0 mmol) and DIEA (6.2 mL, 36.0 mmol) at 0° C. The reaction is allowed to warm to ambient temperature and stirred under nitrogen for 18 hours. After this time, the reaction is evaporated to remove the volatile organics. The resulting residue is treated with water (300 mL) and extracted with a mixture of chloroform/IPA (3:1) (3×300 mL). The combined organic layers are dried over anhydrous sodium sulfate, filtered, and evaporated. The residue is then purified via silica gel chromatography (3-10% MeOH in DCM) to give the title compound (3.5 g, 92.0%). ES/MS m/z 424 (M+H).

Preparation 12 tert-butyl N-[(1R)-1-(methylcarbamoyl)-3-methylsulfanyl-propyl]carbamate

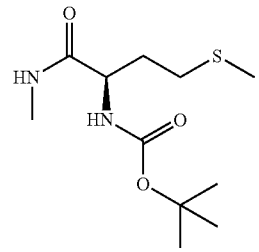 [SMILES: CNC(=O)[C@@H](CCSC)NC(=O)OC(C)(C)C]

Scheme 3, step A: A solution of (tert-butoxycarbonyl)-D-methionine (400 g, 1.6 mol), methyl amine hydrochloride (162.47 g, 2.4 mol), and DIEA (700 mL, 4.01 mol) in DMF (4 L) is cooled to 0° C. and HATU (732.1 g, 1.92 mol) is added. The reaction is warmed to ambient temperature. After 2 hours stirring, the solvent is evaporated. Then water (10 L) is added, and the aqueous solution is extracted with DCM (2×3 L). The organic layers are combined, washed with saturated aqueous sodium bicarbonate (3 L), dried over sodium sulfate, and evaporated. The resulting residue is purified by silica gel chromatography eluting with EtOAc in hexane to give the title compound as a white solid (368 g, 87%). ES/MS m/z 263 (M+H).

Preparation 13 tert-butyl N-[(3R)-1-methyl-2-oxo-pyrrolidin-3-yl] carbamate

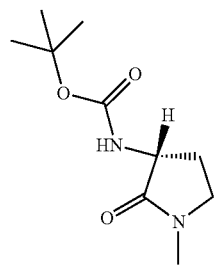

Scheme 3, step B: A mixture of tert-butyl N-[(1R)-1-(methylcarbamoyl)-3-methylsulfanyl-propyl]carbamate (368 g, 1.40 mol) and MeI (3.68 L, 59.11 mol) is stirred at ambient temperature for 18 hours. Then, the mixture is evaporated. A portion of the resulting crude dimethylsulfonium iodide salt (210 g, 0.52 mol) is dissolved in THF (4.7 L), cooled to 0° C. under a nitrogen atmosphere, and LiHMDS (1.00 M solution in THF, 1.16 L, 1.16 mol) is added dropwise. The reaction mixture is then warmed to ambient temperature. After 4 hours, water (2.4 L) is added and the solvent is evaporated to half volume. The mixture is extracted with DCM (2×3 L). The organics are combined and evaporated. The residue is purified by silica gel chromatography eluting with MeOH in DCM to give the title compound as white solid (50 g). ES/MS m/z 215 (M+H). Chiral HPLC: Rt (retention time)=9.13 minutes; LC Column: ChiralPAc IA OD 4.6×250 mm 5 μm; isocratic: 0.1% diethyl amine/hexanes/ethanol (85/15); Column Temp: 25° C.; Flow Rate: 1.0 mL/min. Optical rotation: $[\alpha]_D^{20}$=+53° (C=0.5, MeOH).

Preparation 14

(3R)-3-amino-1-methyl-pyrrolidin-2-one; p-toluene sulphonyl salt

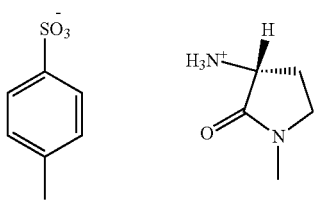

Scheme 3, step C: A mixture of tert-butyl N-[(3R)-1-methyl-2-oxo-pyrrolidin-3-yl]carbamate (46 g, 214.69 mmol) and 4-methylbenzenesulfonic acid (74.5 g, 433 mmol) in acetonitrile (500 mL) is heated at 55° C. and stirred for 4 hours. Then, MTBE (1 L) is added, and the mixture is cooled to 22° C. The resulting solid is collected by filtration, washed with additional MTBE, and dried under vacuum to constant weight to give the title compound as a white solid (60 g, 95%). ES/MS m/z 115 (M+H). Optical rotation: $[\alpha]_D^{20}$=+31.3° (C=0.5, MeOH).

Example 1

5-(2-Methoxyanilino)-7-(methylamino)-N-[(3R)-1-methyl-2-oxo-pyrrolidin-3-yl]pyrazolo[1,5-a]pyrimidine-3-carboxamide

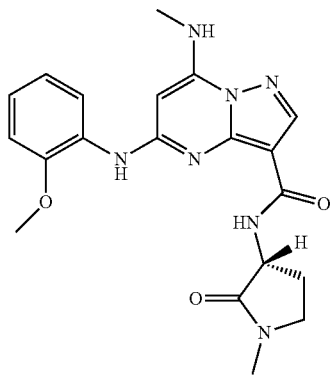 [SMILES: CNc1cc(Nc2ccccc2OC)nc2c(C(=O)N[C@@H]3CCN(C)C3=O)cnn12]

Scheme 4: A mixture of 5-(2-methoxyanilino)-7-(methylamino)pyrazolo[1,5-a]pyrimidine-3-carboxylic acid (50 g, 159.6 mmol) and (3R)-3-amino-1-methyl-pyrrolidin-2-one; p-toluene sulphonyl salt (60 g, 222 mmol) in pyridine (150 ml) is stirred at ambient temperature for 15 min. Then T3P (1.67 M solution in EtOAc, 185 mL, 309 mmol) is added and the mixture is heated at 80° C. for 3 hours. The reaction mixture is cooled to 60° C. and water (600 mL) is added. The reaction is cooled to ambient temperature and the resulting solid is collected by filtration and washed with water (100 mL).

The resulting wet solid is dissolved in DMSO (300 mL) and heated to 60° C. Activated charcoal (2 g) is added and stirred at 60° C. for 30 minutes. The mixture is then filtered over diatomaceous earth. Over the filtrated solution, water (300 mL) is added dropwise keeping temperature at 60° C. The mixture is cooled to ambient temperature, and the resulting solid is collected by filtration and washed with water (100 mL). The solid is dried under vacuum to constant weight to give the title compound as a white solid (52 g, 78%). ES/MS m/z 410 (M+H). Chiral SFC: Rt (retention time)=1.63 minutes; SFC Column: Chiralpak AD (4.6×100 mm) 5 μm; isocratic: IPA (0.2% IPAm); Column Temp: 40° C.; Flow Rate: 5.0 mL/min. Optical rotation: $[\alpha]_D^{20}$=−4.19° (C=0.3, MeOH).

Alternate Example 1

5-(2-Methoxyanilino)-7-(methylamino)-N-[(3R)-1-methyl-2-oxo-pyrrolidin-3-yl]pyrazolo[1,5-a]pyrimidine-3-carboxamide A racemic mixture of 5-(2-methoxyanilino)-7-(methylamino)-N-[rac-1-methyl-2-oxo-pyrrolidin-3-yl]pyrazolo[1,5-a]pyrimidine-3-carboxamide is purified via chiral chromatography to give the first eluting enantiomer as the title compound. ES/MS m/z 410 (M+H). Purification conditions: CHIRALPAK® AD-H; Mobile Phase: 10% ACN in MeOH;

Flow rate: 30 mL/min; UVW: 225 nm; Retention time: 2.53 minutes. (S enantiomer retention time: 3.78 min).

Example 2

5-(2-Ethoxyanilino)-7-(methylamino)-N-[(3R)-1-methyl-2-oxo-pyrrolidin-3-yl]pyrazolo[1,5-a]pyrimidine-3-carboxamide

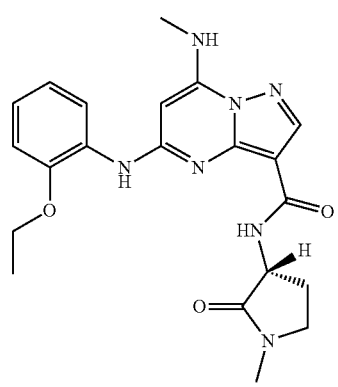 [SMILES: CCOc1ccccc1Nc1cc(NC)n2ncc(C(=O)N[C@@H]3CCN(C)C3=O)c2n1]

A racemic mixture of 5-(2-ethoxyanilino)-7-(methylamino)-N-[rac-1-methyl-2-oxo-pyrrolidin-3-yl]pyrazolo[1,5-a]pyrimidine-3-carboxamide is purified via chiral chromatography to give the first eluting enantiomer as the title compound. ES/MS m/z 424 (M+H). Purification conditions: CHIRALPAK® AD-H; Mobile Phase: 40% EtOH in $CO_2$; Flow rate: 70 g/min; UVW: 260 nm; Retention time: 2.56 minutes. (S enantiomer retention time: 4.28 min).

Binding to TYK2 JH2 by Scintillation Proximity Assay

The pseudokinase domain (JH2) of human JAK (Janus family of cytoplasmic tyrosine kinases) family tyrosine kinase 2 (TYK2) with an N-terminal His[6] tag is expressed in baculovirus and purified by Ni-NTA affinity and size-exclusion chromatography. Yttrium (YSi) His-Tag scintillation proximity assay (SPA) beads (cat #PRNQ0096) are purchased from PerkinElmer Life Sciences. $^3$H—N-[(1R)-1-[3-[8-Methyl-5-(methylamino)-8H-imidazo[4,5-d]thiazolo[5,4-b]pyridin-2-yl]phenyl]ethyl]-2-(methylsulfonyl) benzamide is synthesized by Quotient Bio with a specific activity of 63 Ci/mmol and a concentration 6.78 μM stored in ethanol (cat #TRQ41678) (See also e.g., J. S. Tokarski, et al., *J. Biol. Chem.*, vol. 290(17), pages 11061-11074 (2015) and R. Moslin, et al., *Med. Chem. Commun.*, vol. 8, pages 700-712 (2017)).

A 3 fold, 10 point serial dilution of Example 1 is prepared in 100% DMSO (200 nL) and transferred to a 96 well, white, clear bottom, non-binding surface assay plate (Costar 3604) using acoustic liquid handling. Control wells used to determine percent inhibition contained either DMSO (200 nL) or cold, unlabeled inhibitor (200 nL, 10 mM, 200 μM final concentration). His-tagged TYK2 JH2 (20 μL of 7.1 nM) and $^3$H—N-[(1R)-1-[3-[8-methyl-5-(methylamino)-8H-imidazo[4,5-d]thiazolo[5,4-b]pyridin-2-yl]phenyl]ethyl]-2-(methylsulfonyl) benzamide (50 nM) in assay buffer (50 mM HEPES, pH 7.5, 0.005% Tween-20) are added to the diluted inhibitor. After incubation at room temperature for 2 hours, YSi Copper His-Tag SPA beads (100 μL of 0.5 mg/mL) in phosphate-buffered saline (PBS) containing 0.2% BSA are added to each well. After 15 minutes at room temperature, radioactivity is counted using the Trilux Microbeta. Percent inhibition of radioligand binding at each inhibitor concentration is calculated and fit to the four parameter nonlinear logistic equation using Genedata Screener© to give an $IC_{50}$ for the compound of Example 1 of 0.045 μM (±0.016 μM, n=3) and for the compound of Example 2 of 0.040 μM (±0.012 μM, n=4) expressed as GeoMetric means with the standard error of the mean (SEM). This result demonstrates that the compounds of Example 1 and Example 2 bind to the TYK2 JH2 domain in vitro.

Inhibition of IFNα Signaling Through pSTAT1 in TF1 Cells

TF1 cells (ATCC, CL-2003) are grown in RPMI 1640 (GIBCO) supplemented with 10% dialyzed FBS, 0.1 mg/ml Ampicillin and 2 ng/mL granulocyte macrophage colony stimulating factor. TF1 cells (100 K per well) are seeded in a 96-well poly-D-lysine coated plates in serum-free DMEM and incubated overnight at 37° C. under 5% $CO_2$. Example 1 is serially diluted in DMSO, added to the cells, and incubated at 37° C. for 1 hr. Cells are then stimulated with 10 ng/ml IFNα2 at 37° C. for 20 minutes. After removing the medium, the cells are lysed in buffer containing Halt protease and phosphatase inhibitor cocktail (Thermo Scientific #78441) at room temperature for 30 minutes. The amount of p-Stat1 (Tyr701) is quantified as light emission at 615 nm using the AlphaLISA SureFire Ultra p-Stat1 (Tyr701) assay kit (Perkin Elmer #ALSU-PST1-A50K) following the vendor's recommended protocol. Percent inhibition at each inhibitor concentration is calculated and fit to the four parameter nonlinear logistic equation using Genedata Screener® to give an $IC_{50}$ for the compound of Example 1 of 0.008 μM (±0.001 μM, n=5) and for the compound of Example 2 of 0.010 μM (±0.001 μM, n=4) expressed as GeoMetric means with the standard error of the mean (SEM). This result demonstrates that the compounds of Example 1 and Example 2 are inhibitors of IFNα signaling through pSTAT1 in TF1 cells.

IL23 pSTAT3 AlphaLISA Assay

IL2-dependent Kit225 cells expressing endogenous IL23 receptors are stably transduced with the Lenti STAT3 Reporter linked to firefly luciferase (SABiosciences CLS-6028L). These cells are used to monitor TYK2 activity by quantifying gene expression caused by STAT3 phospory-lation following induction by IL23 in the presence of IL2 using AlphaLISA technology (TGR Biosciences ALSU-TST3-A50K). The cells are grown in RPMI 1640 (Gibco 22400) supplemented with 10% FBS (Invitrogen 10082), 1× Pen/Strep (Gibco 15140-122), 200 ng/ml Puromycin (Sigma P9620), and fresh 10 ng/ml recombinant human IL2 (R&D Systems 202-IL-50).

For assay preparation, cells are dispensed into Biocoat black poly-d-lysine coated clear bottom 384-well plates (Becton Dickinson Bio-Coat 35-4640) in DMEM (Sigma D5796) at 300,000 cells/well and allowed to incubate overnight at 37° C. Compounds solubilized in DMSO are serially diluted 1:3 to produce a 10-point concentration response curve (final DMSO=0.1%). Cells are pre-incubated with Example 1 for 1 hour at 37° C., then stimulated with IL23 (25 ng/ml final) for 30 minutes. After centrifugation at 2000 rpm for 10 minutes, cell pellets are lysed with a mixture of 1:1 lysis buffer (TGR Biosciences) and Halt Protease & Phosphatase inhibitor cocktail (Thermo Scientific 1861281) for 30 minutes. The AlphaLISA reaction is performed following the vendor's recommended protocol, and the luciferase levels are measured using an Envision plate reader (Perkin Elmer). The relative $IC_{50}$ is calculated using a 4-parameter nonlinear logistic equation (GeneData Screener 13.0.5) to give an $IC_{50}$ for the compound of Example 1 of 0.009 μM (±0.001 μM, n=4) and for the compound of Example 2 of 0.010 μM (±0.002 μM, n=3) expressed as GeoMetric means with the standard error of the mean (SEM). This result demonstrates that the compounds of Example 1 and Example 2 are inhibitors of IL-23 signaling in a cell-based assay.

We claim:

1. A compound of the formula:

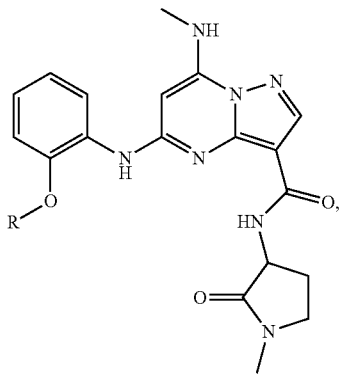

wherein R is methyl or ethyl;
or a pharmaceutically acceptable salt thereof.

2. The compound according to claim 1 wherein R is methyl; or a pharmaceutically acceptable salt thereof.

3. The compound according to claim 1 wherein R is ethyl; or a pharmaceutically acceptable salt thereof.

4. The compound according to claim 1 wherein the compound is:

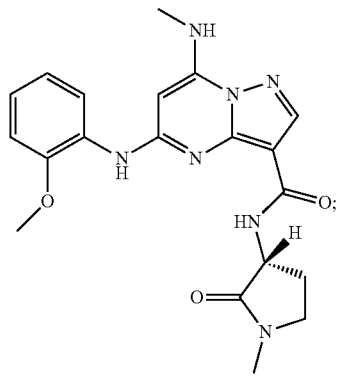 [SMILES: CNc1cc(Nc2ccccc2OC)nc2c(C(=O)N[C@@H]3CCN(C)C3=O)cnn12]

or a pharmaceutically acceptable salt thereof.

5. The compound according to claim 4 wherein the compound is:

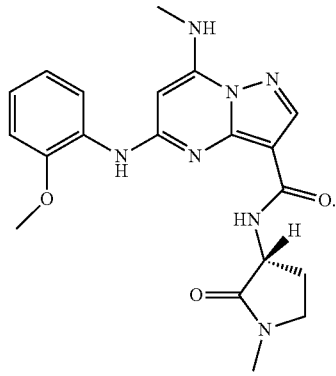 [SMILES: CNc1cc(Nc2ccccc2OC)nc2c(C(=O)N[C@@H]3CCN(C)C3=O)cnn12]

6. The compound according to claim 1 wherein the compound is:

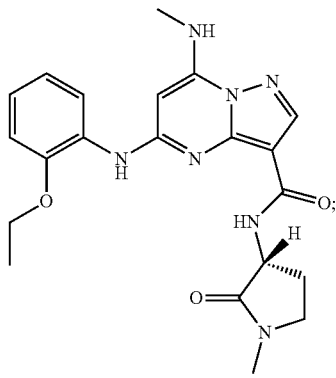 [SMILES: CCOc1ccccc1Nc1cc(NC)n2ncc(C(=O)N[C@@H]3CCN(C)C3=O)c2n1]

or a pharmaceutically acceptable salt thereof.

7. The compound according to claim 6 wherein the compound is:

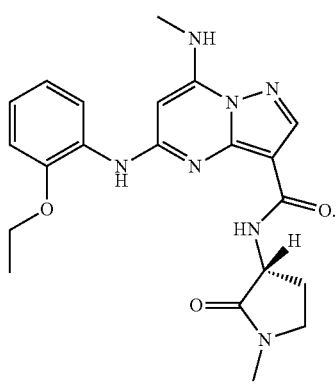 [SMILES: CCOc1ccccc1Nc1cc(NC)n2ncc(C(=O)N[C@@H]3CCN(C)C3=O)c2n1]

8. A method of treating psoriasis in a patient, comprising administering to a patient in need of such treatment an effective amount of a compound according to claim 1, or a pharmaceutically acceptable salt thereof.

9. A method of treating systemic lupus erythematosus in a patient, comprising administering to a patient in need of such treatment an effective amount of a compound according to claim 1, or a pharmaceutically acceptable salt thereof.

10. A pharmaceutical composition, comprising a compound or a pharmaceutically acceptable salt thereof, according to claim 1 with one or more pharmaceutically acceptable carriers, diluents, or excipients.

11. A process for preparing a pharmaceutical composition, comprising admixing a compound or a pharmaceutically acceptable salt thereof according to claim 1 with one or more pharmaceutically acceptable carriers, diluents, or excipients.

\* \* \* \* \*